US00PP28017P3

(12) United States Plant Patent
Olesen

(10) Patent No.: US PP28,017 P3
(45) Date of Patent: May 16, 2017

(54) MINIATURE ROSE PLANT NAMED 'POULPAH072'

(50) Latin Name: ***Rosa* hybrid**
Varietal Denomination: Poulpah072

(71) Applicant: Mogens Nyegaard Olesen, Fredensborg (DK)

(72) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 14/756,271

(22) Filed: Aug. 20, 2015

(65) Prior Publication Data

US 2017/0055391 P1 Feb. 23, 2017

(51) Int. Cl.
*A01H 5/02* (2006.01)

(52) U.S. Cl.
USPC ..... Plt./121

(58) Field of Classification Search
USPC ..... Plt./121
See application file for complete search history.

(56) References Cited

PUBLICATIONS

Indoor Roses by Poulsen Main Varieties 2013.*
PLUTO Plant Variety Database Aug. 10, 2016.*

* cited by examiner

*Primary Examiner* — Annette Para

(57) ABSTRACT

A new garden rose plant of the miniature class which has abundant, pink flowers and attractive foliage. This new and distinct variety has shown to be uniform and stable in the resulting generations from asexual propagation.

1 Drawing Sheet

Botanical designation: *Rosa* hybrid.
Variety denomination: 'Poulpah072'.

SUMMARY OF THE INVENTION

The present discovery constitutes a new and distinct variety of miniature rose plant which was discovered in a cultivated area. The new rose variety resulted from a naturally occurring mutation of unknown causation on a branch of 'Poulpah059', U.S. Plant Pat. No. 24,850. The resulting mutation was selected and evaluations were conducted on the resulting rose plants in a controlled environment.

The rose plant of the present discovery has a unique combination of characteristics which are outstanding in the new variety and which distinguish it from the original rose 'Poulpah059' as well as all other varieties which we are aware of. For example, 'Pou1pah059' has a general tonality of flower color Orange Group 25 A, later becoming Yellow Group 11C as flowers mature. 'Pou1pah072' as a general tonality of flower which is Red Group 51C.

The criteria used to evaluate the claimed plant were selected in order to introduce a distinct variety for garden use with unique qualities, such as:

1. Uniform and abundant pink flowers;
2. Vigorous, but compact growth when propagated both as a budded rose and on its own roots;
3. Exceptional disease resistance.

This combination of qualities is not present in previously available commercial cultivars of this type, known to the inventor, and distinguish 'Poulpah072' from all other varieties of which we are aware.

Asexual reproduction of 'Poulpah072' by vegetative cuttings was first done by Mogens N. Olesen in Fredensborg, Denmark, in July of 2007. This initial and other subsequent propagations have demonstrated that the characteristics of 'Poulpah072' are stable and reproduced true to type in successive generations of asexual reproduction.

DESCRIPTION OF THE DRAWING

The accompanying color illustration shows as true as is reasonably possible to obtain in color photographs of this type, the typical characteristics of the buds, flowers, leaves, and stems, of 'Poulpah072'.

Specifically illustrated are open flowers, a cluster of open flowers, showing pedicels and peduncles, juvenile growth exhibiting anthocyanin, bare stem with prickles, flower petals detached, sepals detached, and reproductive flower parts. Plants shown are 1 year old.

DETAILED DESCRIPTION OF THE VARIETY

The following is a description of 'Poulpah072', as observed in its growth outdoors in Odense Denmark. Observed plants are 1 year old, and were grown on their own roots in 23 cm containers. Color references are made using The Royal Horticultural Society (London, England) Colour Chart, 2001, except where common terms of color are used.

For a comparison, several physical characteristics of the rose variety 'Poulhi008', U.S. Plant Pat. No. 15,722 are compared to 'Poulpah072' in Chart 1.

Chart 1

| | 'Poulpah072' | 'Poulhi008' |
|---|---|---|
| Petal Count | 70 | 40 to 45 |
| Flower Diameter | 70 to 80 mm | 80 mm |
| General Tonality of Flower Color | Red Group 51C | Red Group 55B |

Flower and Flower Bud

Blooming habit: Continuous.

Flower bud:

*Size*.—Upon opening, 20 mm in length from base of receptacle to end of bud. Bud diameter is 12 mm.

*Bud form*.—Ovoid.

*Bud color*.—As sepals divide petals are Red Group 48C.

*Sepal inner surface*.—Color: Yellow-Green Group 146C. Surface: Lightly pubescent.

*Sepal outer surface*.—Color: Yellow-Green Group 146D with intonations of Greyed-Purple Group 183D. Texture: Somewhat rough.

*Sepal shape*.—Apex: Cirrhose. Base: Flat at union with receptacle.

*Sepal margin*.—Margins have weak foliaceous appendages on three of the five sepals.

*Sepal size*.—15 mm long, 10 mm wide.

*Receptacle*.—Texture: Smooth. Size: 5 mm in height, 11 mm wide. Color: Yellow-Green Group 144C with intonations of Greyed-Purple Group 184C. Shape: Broad funnel.

*Pedicel*.—Surface: Somewhat rough with many stipitate glands. Length: Range from 10 to 60 mm. Diameter: 3 mm on average. Color: Yellow-Green Group 146B with light intonations of Greyed-Red Group 180D. Strength: Moderate.

*Peduncle*.—Length: 4 to 16 cm. Diameter: About 4 mm. Color: Yellow-Green Group 146A. Texture: Smooth.

Flower bud development: Flower buds are borne in panicles of 3 to 15 flower buds per stem.

Flower bloom:

*Fragrance*.—Strong perfume.

*Duration*.—The blooms have a duration on the plant of approximately 10 days. Petals fall cleanly away from plant after flowers have fully matured.

*Size*.—Flower diameter is 70 to 80 mm when open. Flower depth is about 30 mm.

*Flower shape*.—Rosette. Very double flower with many slightly overlapping petals of different sizes. Shape of flower, side view: The upper portion is flat. The lower portion is a flattened convex.

Petalage: Under normal conditions, flowers have 70 petals total, 25 of which are petaloids.

General tonality of flower: Open flowers are Red Group 51C.

Petal color:

*Upon opening, inner and outer petals*.—Upper surface: Red Group 51C. Lower surface: Red Group 51C.

*Basal petal spots, upon opening*.—Upper surface: Yellow Group 10B. Lower surface: Yellow Group 10C.

*After opening, inner and outer petals*.—Upper surface: Red Group 51C. Lower surface: Red Group 51C.

*Basal petal spots, after opening*.—Upper surface: Yellow Group 10B. Lower surface: Yellow Group 10C.

Petals:

*Petal reflex*.—Weak.

*Margin*.—Entire and uniform. Weak undulations.

*Shape*.—Generally broad elliptic. Apex shape: Rounded. Base shape: Rounded.

*Size*.—35 mm (l)×35 mm (w).

*Texture*.—Smooth.

*Thickness*.—Average.

Petaloids:

*Size*.—About 15 mm (l) by 10 mm (w).

*Quantity*.—Normally 25.

*Shape*.—Irregular, asymmetric. The apex is rounded, or acute. The base is acute.

*Color*.—The upper and lower surface is Red Group 51C. Petaloid spots are Yellow Group 10B on upper and lower surface.

Reproductive flower parts:

*Pollen*.—None observed.

*Anthers*.—Size: 3 mm in length. Color: Orange-Red Group 32B. Quantity: 80 on average.

*Filaments*.—Color: Yellow-Orange Group 22A. Length: 7 mm.

*Pistils*.—Length: 3 mm. Quantity: About 60.

*Stigmas*.—Color: Yellow Group 10B.

*Styles*.—Color: Green-Yellow Group 1B.

*Location of stigmas*.—Inferior in location relative to the length of the filaments and the height of the anthers.

*Hips*.—None Observed.

Plant

Plant growth: Upright, bushy. Plants are 35 cm in height, and 35 cm wide.

Stems:

*Color*.—Juvenile growth: Yellow-Green Group 144B. Mature growth: Yellow-Green Group 146A.

*Length*.—On average, canes are 30 cm from the base of the plant to the flowering portion.

*Diameter*.—7 mm.

*Internodes*.—On mature canes about 35 mm between nodes.

*Surface texture*.—Young wood: Smooth. Older wood: Smooth.

Long prickles:

*Incidence*.—From 3 to 12 prickles per 10 cm of stem.

*Size*.—Average length of prickles on mature stems is 6 mm.

*Shape*.—Upper portion is concave. Lower portion is deep concave.

*Color*.—Juvenile prickles: Greyed-Red Group 181C. Mature prickles: Greyed-Red Group 181C.

Plant foliage:

*Compound leaf*.—About 145 mm (l)×115 (w).

*Quantity*.—2 leaves per 10 cm of stem on average.

*Leaf bearing angle to the stem*.—45 degrees.

*Color of juvenile foliage*.—Upper side: Greyed-Purple Group 185A. Lower side: Greyed-Purple Group 185A.

*Color of mature foliage*.—Upper side: Yellow-Green Group 147A. Lower side: Yellow-Green Group 147B.

Plant leaves and leaflets:

*Stipules*.—Size: 20 mm long, 8 mm wide. Quantity: 2 per compound leaf. Shape: Linear, slightly broad based with outward extending apices. Margins: Finely serrated. Color: Yellow-Green Group 147A with intonations of Greyed-Purple Group 184D on some stipules.

*Petiole*.—Length: About 30 mm. Diameter: 2 mm.

*Upper surface*.—Color: Yellow-Green Group 146A with intonations of Greyed-Red Group 179A on some petioles.

*Lower surface*.—Color: Yellow-Green Group 144A.

*Rachis*.—Length: 20 to 25 mm. Upper surface: Color: Yellow-Green Group 146A with intonations of Greyed-Red Group 179A on some rachis.

*Lower surface*.—Color: Yellow-Green Group 144A.

*Leaflet*.—Quantity: Normally 5 leaflets. Margins: Serrated. Size: On average terminal leaflets are 60 mm long, 45 mm wide. Shape: Generally ovate. Base: Rounded. Apex: Acute. Texture: Smooth. Thickness: Average. Arrangement: Odd pinnate. Venation: Reticulate. Glossiness: Moderately glossy.

Disease resistance: Above average resistance to powdery mildew *Sphaerotheca pannosa*, downy mildew *Peronospora sparsa*, rust *Phragmidium* sps., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the miniature rose class named 'Poulpah072', substantially as illustrated and described herein, due to its abundant pink flowers, disease resistance, and extended period of bloom.

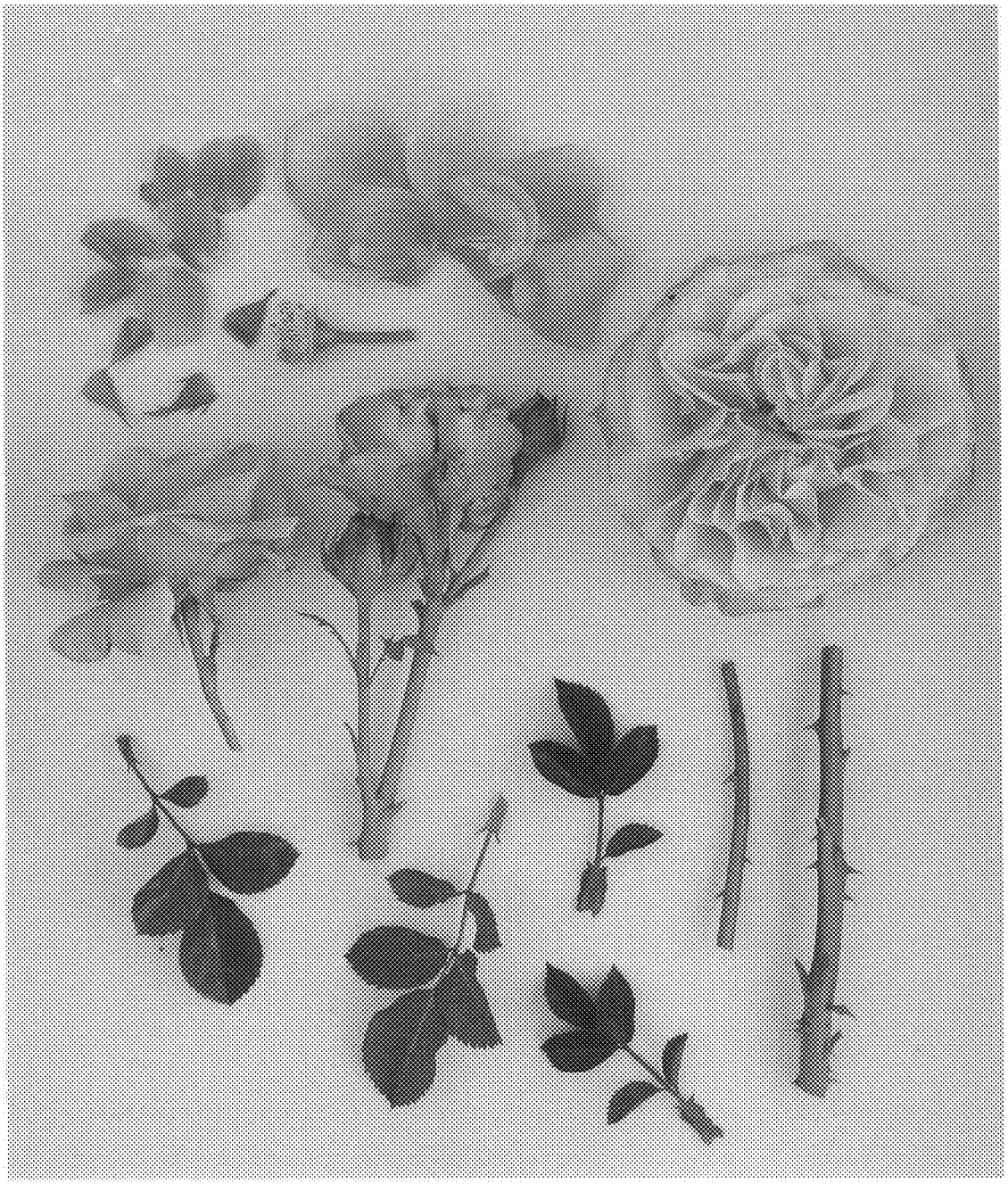

* * * * *